United States Patent
Fang et al.

(10) Patent No.: US 6,869,786 B1
(45) Date of Patent: Mar. 22, 2005

(54) **METHOD FOR CLONING AND EXPRESSION OF BSRGI RESTRICTION ENDONUCLEASE AND BSRGI METHYLTRANSFERASE IN *E. COLI***

(75) Inventors: Ningyuan Fang, Beverly, MA (US); Shuang-yong Xu, Lexington, MA (US)

(73) Assignee: New England Biolabs, Inc., Beverly, MA (US)

( * ) Notice: Subject to any disclaimer, the term of this patent is extended or adjusted under 35 U.S.C. 154(b) by 242 days.

(21) Appl. No.: 10/338,898

(22) Filed: Jan. 8, 2003

(51) Int. Cl.[7] ............................. C12N 9/22; C12N 15/55
(52) U.S. Cl. ................. 435/199; 435/252.3; 435/320.1; 536/23.2
(58) Field of Search ............................. 435/199, 252.3, 435/320.1; 536/23.2

(56) References Cited

U.S. PATENT DOCUMENTS

| | | | |
|---|---|---|---|
| 5,200,333 A | 4/1993 | Wilson | 435/6 |
| 5,498,535 A | 3/1996 | Fomenkov et al. | 435/6 |

OTHER PUBLICATIONS

Roberts and Macelis, Nucl. Acids Res. 29:268–269 (2001).
Kosykh et al., Mol. Gen. Genet. 178: 717–719, (1980).
Mann et al., Gene 3: 97–112, (1978).
Walder et al., Proc. Natl. Acad. Sci. 78: 1503–1507, (1981).
Bougueleret et al., Nucl. Acids Res. 12: 3659–3676, (1984).
Gingeras and Brooks, Proc. Natl. Acad. Sci. USA 80: 402–406, (1983).
Theriault and Roy, Gene 19: 355–359 (1982).
Blumenthal et al., J. Bacteriol. 164: 501–509, (1985).
Wayne et al. Gene 202: 83–88, (1997).
Kiss et al., Nucl. Acids Res. 13: 6403–6421, (1985).
Szomolanyi et al., Gene 10: 219–225, (1980).
Janulaitis et al., Gene 20: 197–204 (1982).
Kiss and Baldauf, Gene 21: 111–119, (1983).
Walder et al., J. Biol. Chem. 258: 1235–1241, (1983).
Fomenkov et al., Nucl. Acids Res. 22: 2399–2403 (1994).
Malone et al., J. Mol. Biol. 253: 618–632, (1995).
New England Biolabs' Catalog, 2000–01, p. 220.
Kong, et al., Nucl. Acids. Res. 28:3216–3223 (2000).

*Primary Examiner*—Charles L. Patterson, Jr.
(74) *Attorney, Agent, or Firm*—Gregory D. Williams; Harriet M. Strimpel

(57) ABSTRACT

The present invention relates to recombinant DNA encoding the BsrGI restriction endonuclease as well as BsrGI methyltransferase, expression of BsrGI restriction endonuclease and BsrGI methyltransferase in *E. coli* cells containing the recombinant DNA.

6 Claims, 11 Drawing Sheets

Figure 2

```
     ATGATTGATTTAAATAAAGTTAGAATTTCTCTTCAAGACGAGAAGTCTAATCTTTCTAAA     60
  1  ------+---------+---------+---------+---------+---------+
      M  I  D  L  N  K  V  R  I  S  L  Q  D  E  K  S  N  L  S  K

ATGTCTAAGGAATTGATTCATATTTCTATTTAAGGCTTCTAAACCCGCAAGAAAGTTTA    120
 61  ------+---------+---------+---------+---------+---------+
      M  S  K  E  L  I  H  I  F  Y  L  R  L  L  N  P  Q  E  S  L

AAGCAAATAAAGACAATTGGGAAAAAGAATTTAATTTATATGGCGATAAAAAAT        180
121  ------+---------+---------+---------+---------+---------+
      K  Q  I  K  D  N  W  E  K  E  F  N  F  I  Y  G  D  I  K  N

AATTTTCGAGCAATAAAAAGGTCGATGTGTTTTGTCTGTTTATGCAATACAGACATACTTTAGC    240
181  ------+---------+---------+---------+---------+---------+
      N  F  S  S  N  K  K  V  K  P  Q  E  L  A  N  T  Y  S  I  N

ACTGAAAATGGAGAGTCGATGTGTTTTGTCTGTTTATGCAATACAGACATACTTTAGC    300
241  ------+---------+---------+---------+---------+---------+
      T  E  N  G  E  V  D  V  F  C  L  F  Y  A  I  Q  T  Y  F  S

TTATTTATAAAATTACTAACCTACAAACTATTAAGCGGTATCAAAGAAGATAAAGTAAGT    360
301  ------+---------+---------+---------+---------+---------+
      L  F  I  K  L  L  T  Y  K  L  L  S  G  I  K  E  D  K  V  S

TTCGAAAATTACAATTTTAGGGAGTTTATAGTTTTCTATTTTACATGGCAGTTATTTTGAG    420
361  ------+---------+---------+---------+---------+---------+
      F  E  N  Y  N  F  R  E  F  I  V  S  I  L  H  G  S  Y  F  E
```

Figure 2 (continued)

```
      AATCTAGGGATTGAAAACTACTGTTATACAGATTGGTTTTGTTGGATAGATGAATGTTTA
421   ------+---------+---------+---------+---------+---------+   480
      ------+---------+---------+---------+---------+---------+
       N  L  G  I  E  N  Y  C  Y  T  D  W  F  C  W  I  D  E  C  L

GACAATGAAATAGAGAGTAAATTTTTAATTTATTACAGGAATTAAACAAATTTGATGAG
481   ------+---------+---------+---------+---------+---------+   540
      ------+---------+---------+---------+---------+---------+
       D  N  E  I  E  S  K  I  F  N  L  Q  E  L  N  K  F  D  E

ATTAATAACTTACAGGAATTTATTTCAATTCACAATAACGATAATATCAAACAAATGTAT
541   ------+---------+---------+---------+---------+---------+   600
      ------+---------+---------+---------+---------+---------+
       I  N  N  L  Q  E  F  I  S  I  H  N  N  D  N  I  K  Q  M  Y

GAAATTATTATACCTCGCCAATTAAGGCATGCTCTTGGTGAATACTATACTCCCGATTGG
601   ------+---------+---------+---------+---------+---------+   660
      ------+---------+---------+---------+---------+---------+
       E  I  I  P  R  Q  L  R  H  A  L  G  E  Y  Y  T  P  D  W

TTAGCATTGTATACTATAGAAAATGTAATAGAATTAAGTAAAAAAGAAGTTGAGGAGTTT
661   ------+---------+---------+---------+---------+---------+   720
      ------+---------+---------+---------+---------+---------+
       L  A  L  Y  T  I  E  N  V  I  E  L  S  K  K  E  V  E  E  F

AACAAAACTTATTTAGACCCAACATGTGGTTCTGGTACATTTTTATTTAAAACAATACAA
721   ------+---------+---------+---------+---------+---------+   780
      ------+---------+---------+---------+---------+---------+
       N  K  T  Y  L  D  P  T  C  G  S  G  T  F  L  F  K  T  I  Q

CGTTTAAGAAAAAGTGATATAAAATTGAATAAGATTATATATTCAGTAAGGGGATTTGAT
781   ------+---------+---------+---------+---------+---------+   840
      ------+---------+---------+---------+---------+---------+
       R  L  R  K  S  D  I  K  L  N  K  I  I  Y  S  V  R  G  F  D
```

Figure 2 (continued)

```
     GTAAATCCAATAGCAGTATTAACTGCTAAGACTAATTAATATCAATAATTGATTTA
     ------+---------+---------+---------+---------+---------+  900
841                                                                
      V  N  P  I  A  V  L  T  A  K  T  N  Y  L  I  S  I  D  L

ATAAAAGATAAGACCGTAATAAATTTACCCTGTTTATAACTATGATGTAATTCACCA
     ------+---------+---------+---------+---------+---------+  960
901                                                                
      I  K  D  K  T  V  I  N  L  P  V  Y  N  Y  D  V  I  N  S  P

ATATTAAAAGAAAATAAACTTCTTTCTGTTGATATAAATGTTATTACAATATTCCG
     ------+---------+---------+---------+---------+---------+  1020
961                                                                
      I  L  K  E  N  K  L  L  S  V  D  I  N  N  V  I  Y  N  I  P

TTATCAATTTTAAAGGATGAGCATTTTAAACCTTTAAAAAATATTAATACAATCATTA
     ------+---------+---------+---------+---------+---------+  1080
1021                                                               
      L  S  I  L  K  D  E  H  F  K  T  F  K  K  I  L  I  Q  S  L

AAAAGTAACTTGAATCCTGAAGAGTTTTATAACCTTCTTTTGGAACAAAAAATAAATCTA
     ------+---------+---------+---------+---------+---------+  1140
1081                                                               
      K  S  N  L  N  P  E  E  F  Y  N  L  L  L  E  Q  K  I  N  L

AAAAATAAGGCAGAAGTGATTGAGTTTTATTCTAAATTAATAGTACAAATATAAAA
     ------+---------+---------+---------+---------+---------+  1200
1141                                                               
      K  N  K  A  E  V  I  E  F  Y  S  K  L  L  N  S  T  N  I  K

ATACGACTAATAATTGCTTATTTATTAATTAATCGTTTAGAAGCTTATATAAACTAGATAGA
     ------+---------+---------+---------+---------+---------+  1260
1201                                                               
      I  R  L  I  I  A  Y  L  L  I  N  R  L  E  A  Y  K  L  D  R
```

Figure 2 (continued)

```
       GTCGATATTATAATAGGAAATCCACCTTGGGTTAACTGGGAGTACCTTCCTAAGGAGTAT
1261   ------------------------------------------------------------   1320
       V  D  I  I  I  G  N  P  P  W  V  N  W  E  Y  L  P  K  E  Y

AGAGAAAAATCTCAACACCTCTGGGTAGAATATGGTCTTTTTGCTATGAAGGGAGAGAT
1321   ------------------------------------------------------------   1380
       R  E  K  S  Q  H  L  W  V  E  Y  G  L  F  A  M  K  G  R  D

TTAAGTTTCTCGAAAAGAGATATATTTCAATTCTTATAACTTATTTAGTTATTGATAAATTT
1381   ------------------------------------------------------------   1440
       L  S  F  S  K  E  D  I  S  I  L  I  T  Y  L  V  I  D  K  F

CTCAAAGATTATGGACATTTAGCATTTGTTATAAGACAAGGTATTTTCAAATCTGCAAAA
1441   ------------------------------------------------------------   1500
       L  K  D  Y  G  H  L  A  F  V  I  R  Q  G  I  F  K  S  A  K

AACGGTATAGGTTTTAGAAGGTTTCAAGTTGGAAATGATTACTATCTAAAAGTAAAAAGA
1501   ------------------------------------------------------------   1560
       N  G  I  G  F  R  R  F  Q  V  G  N  D  Y  Y  L  K  V  K  R

GTAGATGACCTCTCCTTCATTAAACCATTTGAAAAATGCAACTAATAGTACATCTGTGTTA
1561   ------------------------------------------------------------   1620
       V  D  D  L  S  F  I  K  P  F  E  N  A  T  N  S  T  S  V  L

TTCTTACAAAAGAATCATAAAACAGAATATCCAGTTCCATATTATGTTTGGAAAAAAAGA
1621   ------------------------------------------------------------   1680
       F  L  Q  K  N  H  K  T  E  Y  P  V  P  Y  Y  V  W  K  K  R
```

Figure 2 (continued)

```
                AATTCCGTTTCTAAATTAACTTTAAGAACATATGATGAGTTGTCAGATATACTAACAAAC
      1681      ------+---------+---------+---------+---------+---------+      1740
                 N  S  V  S  K  L  T  L  R  T  Y  D  E  L  S  D  I  L  T  N

GTAGATATAAAGAAATGATAGCATTCCTTCTGATAAAAATGATGAGACATCCTTATGG
      1741      ------+---------+---------+---------+---------+---------+      1800
                 V  D  I  K  E  M  I  A  F  P  S  D  K  N  D  E  T  S  L  W

ATAACAATACCAGAGAAAACACTTTCTGTGATTACCAATGTACTAGGTACAAACAGTTAT
      1801      ------+---------+---------+---------+---------+---------+      1860
                 I  T  I  P  E  K  T  L  S  V  I  T  N  V  L  G  T  N  S  Y

AAGGCGAGAACAGGTGTTTTTCACTGGGGGTGCCAACGCTGTATACTGGTTGGAAATTAAA
      1861      ------+---------+---------+---------+---------+---------+      1920
                 K  A  R  T  G  V  F  T  G  G  A  N  A  V  Y  W  L  E  I  K

GATAAAAGACAATGGTAAAATACTAG
      1921      ------+---------+-------+      1947
                 D  K  K  T  M  V  K  Y  *
```

Figure 3

```
    ATGAAAAGAATACAAGAGTTTTGGTATTGTGTTGCTTCTCAAGAAGAATTACCTCTGTAT
1   ------+---------+---------+---------+---------+---------+    60
    M  K  R  I  Q  E  F  W  Y  C  V  A  S  Q  E  E  L  P  L  Y

AAGGGGCACGAAATTAGCTCTTCTGTATGTGATAATCTTTCTGCTTTTATTGAACATTAT
61  ------+---------+---------+---------+---------+---------+   120
    K  G  H  E  I  S  S  V  C  D  N  L  L  A  F  I  E  H  Y

AAAGAAGAAGTTAGTAAAGGGAAAAACCTAAAAACCTTTCTCTCAGAAGCCTTAATTAAA
121 ------+---------+---------+---------+---------+---------+   180
    K  E  E  V  S  K  G  K  N  L  K  T  F  L  S  E  A  L  I  K

AAACCTTCGATTAATCATTAACCATTTAAGGTTGCTATTAGGAATCTCTGACAAGAGCTTTAC
181 ------+---------+---------+---------+---------+---------+   240
    K  P  S  I  N  H  L  R  L  L  G  I  S  D  K  R  L  Y

CTTGATTTAACATTCATTTTTAATAGAGCTACCACAGATAATGGTGAAAGATTATAAAT
241 ------+---------+---------+---------+---------+---------+   300
    L  D  L  T  F  F  F  N  R  A  T  T  D  N  G  E  R  L  L  N

GAATCTAGAGAAAATTTAGTTAAACATGATACTAAATTTTTCATTAATCAACTTACCAAT
301 ------+---------+---------+---------+---------+---------+   360
    E  S  R  E  N  L  V  K  H  D  T  K  F  F  I  N  Q  L  T  N

TCTGATAAAAAGAGCATTTCTCTCGTTTAATCACTGATTATTTTATTAATAGAGGAATT
361 ------+---------+---------+---------+---------+---------+   420
    S  D  K  K  E  H  F  S  R  L  I  T  D  Y  F  I  N  R  G  I
```

Figure 3 (continued)

```
     GAAGATATTATTCACATCTTTTCCAGAATGGATAAAAATCAAATAACTTCTATTTTTAAC
421  ------+---------+---------+---------+---------+---------+  480
      E  D  I  I  H  I  F  S  R  M  D  K  N  Q  I  T  S  I  F  N

AATCTAATTGCTCCTAAAGAGATACAGCAAAACAGGCAAAATATCGTGGTCATGGTGCA
481  ------+---------+---------+---------+---------+---------+  540
      N  L  I  A  P  K  E  I  Q  Q  K  Q  A  K  Y  R  G  H  G  A

GAAATGGCCTTCGCTAAAATATTTCATGATTGTGGTGTTACTATTGTCCCAGAAAATAAA
541  ------+---------+---------+---------+---------+---------+  600
      E  M  A  F  A  K  I  F  H  D  C  G  V  T  I  V  P  E  N  K

CACATCAATCCAATGGCAGGATATGACCCAAATGTAGATTTGACTAATATGACAATAGTA
601  ------+---------+---------+---------+---------+---------+  660
      H  I  N  P  M  A  G  Y  D  P  N  V  D  L  T  N  M  T  I  V

CCCAGAAACGCTGCAAATCGGAACATTCATAGCTTCGATTTAGTTGTGAAGGATAATGAA
661  ------+---------+---------+---------+---------+---------+  720
      P  R  N  A  A  N  R  N  I  H  S  F  D  L  V  V  K  D  N  E

GGTAATATCAGAGTACTAGTTCAATCTCTTGAAATCACTCTTCTGACCCTGGTCAGTATGGC
721  ------+---------+---------+---------+---------+---------+  780
      G  N  I  R  V  L  V  Q  S  L  I  H  S  S  D  P  G  Q  Y  G

GTTAACAAATCTGATGAAACTCTTGAAATAAAGAAGTTAACAATTATAATTCAAGA
781  ------+---------+---------+---------+---------+---------+  840
      V  N  K  S  D  E  T  L  E  I  K  K  L  I  N  N  Y  N  S  R
```

Figure 3 (continued)

```
     AATTCACAAAAACCGGTGTATTTACTAGGTTCAGTAGATGGAGTAGGTTTTTGTGAGAAC
841  ------------------------------------------------------------ 900
     N  S  Q  K  P  V  Y  L  L  G  S  V  D  G  V  G  F  C  E  N

CCAAATGGTACAATAGTCAAAATGATAGATGTTTTTGATGATTCTTTCAAATAAATACT
901  ------------------------------------------------------------ 960
     P  N  G  T  I  V  K  M  I  D  V  F  D  D  F  F  Q  I  N  T

CTATTTAAAATCCCAATATTTCTTCAAAAAATTGGGTTAATTGATAATGTTAAAGGAATT
961  ------------------------------------------------------------ 1020
     L  F  K  I  P  I  F  L  Q  K  I  G  L  I  D  N  V  K  G  I

AAGTTTGATACCGATTTCTTCGATGAACATGTAATAGAATACTTTGAAAAAACTTATCTT
1021 ------------------------------------------------------------ 1080
     K  F  D  T  D  F  F  D  E  H  V  I  E  Y  F  E  K  T  Y  L

AAACCAGCGAATATACAAAATCTAACTAACAGTAATTGTAATTTTACTAATTATATAAAA
1081 ------------------------------------------------------------ 1140
     K  P  A  N  I  Q  N  L  T  N  S  N  C  N  F  T  N  Y  I  K

GCTGGAAAAGGTACAGTAATTTTTAAGTAA
1141 ------------------------------ 1170
     A  G  K  G  T  V  I  F  K  *
```

METHOD FOR CLONING AND EXPRESSION OF BSRGI RESTRICTION ENDONUCLEASE AND BSRGI METHYLTRANSFERASE IN E. COLI

BACKGROUND OF THE INVENTION

The present invention relates to recombinant DNA that encodes the BsrGI restriction endonuclease (BsrGI endonuclease or BsrGI) as well as BsrGI methyltransferase (BsrGI methylase or M.BsrGI) and to the expression of BsrGI endonuclease and/or methylase in *E. coli* cells containing the recombinant DNA.

BsrGI endonuclease is found in the strain of *Bacillus stearothermophilus* GR75 (New England Biolabs' strain collection). It recognizes the double-stranded symmetric DNA sequence 5' T/GTACA 3' (/ indicates the cleavage position) and cleaves between the T and G to generate 4-base 5' overhang ends. BsrGI methylase (M.BsrGI) is also found in the same strain, which recognizes the same DNA sequence and presumably modifies hemi-methylated or non-methylated BsrGI sites.

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') along the DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and twenty-eight restriction endonucleases with unique specificities have been identified among the many hundreds of bacterial species that have been examined to date (Roberts and Macelis, *Nucl. Acids Res.* 29:268–269 (2001)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5' TTT/AAA 3', 5' PuG/GNCCPy 3' and 5' CACNNN/GTG 3' respectively. *Escherichia Coli* RY13, on the other hand, produces only one enzyme, EcoRI, which recognizes the sequence 5' G/AATTC 3'.

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., *Mol. Gen. Genet.* 178:717–719, (1980); HhaII: Mann et al., *Gene* 3:97–112, (1978); PstI: Walder et al., *Proc. Nat. Acad. Sci.* 78:1503–1507, (1981)). Since the expression of restriction-modification systems in bacteria enables them to resist infection by bacteriophages, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., *Nucl. Acids. Res.* 12:3659–3676, (1984); PaeR7: Gingeras and Brooks, *Proc. Natl. Acad. Sci. USA* 80:402–406, (1983), Therlault and Roy, *Gene* 19:355–359 (1982); PvuII: Blumenthal et al., *J. Bacteriol.* 164:501–509, (1985); Bsr45I: Wayne et al. *Gene* 202:83–88, (1997)).

A third approach is to select for active expression of methylase genes (methylase selection) (U.S. Pat. No. 5,200,333 and BsuRI: Kiss et al., *Nucl. Acids. Res.* 13:6403–6421 (1985)). Since restriction-modification genes are often closely linked together, both genes can often be cloned simultaneously. This selection does not always yield a complete restriction system however, but instead yields only the methylase gene (BspRI: Szomolanyi et al., *Gene* 10:219–225, (1980); BcnI: Janulaitis et al., *Gene* 20:197–204 (1982); BsuRI: Kiss and Baldauf, *Gene* 21:111–119, (1983); and BsrI; Walder et al., *J. Biol. Chem.* 258:1235–1241, (1983)).

A more recent method, the "endo-blue method", has been described for direct cloning of thermostable restriction endonuclease genes into *E. coli* based on the indicator strain of *E. coli* containing the dinD::lacZ fusion (Fomenkov et al., U.S. Pat. No. 5,498,535; Fomenkov et al., *Nucl. Acids Res.* 22:2399–2403 (1994)). This method utilizes the *E. coli* SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535). The disadvantage of this method is that some positive blue clones containing a restriction endonuclease gene are difficult to culture due to the lack of the cognate methylase gene.

There are three major groups of DNA methyltransferases based on the position and the base that is modified (C5 cytosine methylases, N4 cytosine methylases, and N6 adenine methylases). N4 cytosine and N6 adenine methylases are amino-methyltransferases (Malone et al. *J. Mol. Biol.* 253:618–632 (1995)). When a restriction site on DNA is modified (methylated) by the methylase, it is resistant to digestion by the cognate restriction endonuclease. Sometimes methylation by a non-cognate methylase can also confer DNA sites resistant to restriction digestion. For example, Dcm methylase modification of 5' CCWGG 3' (W=A or T) can also make the DNA resistant to PspGI restriction digestion. Another example is that CpM methylase can modify the CG dinucleotide and make the NotI site (5' GCGGCCGC 3') refractory to NotI digestion (New England Biolabs' catalog, 2000-01, page 220). Therefore methylases can be used as a tool to modify certain DNA sequences and make them resistant to cleavage by restriction enzymes.

Type II methylase genes have been found in many sequenced bacterial genomes (GenBank, http://www.ncbi.nlm.nih.gov; and Rebase™, http://rebase.neb.com/rebase). Direct cloning and over-expression of ORFs adjacent to the methylase genes have yielded restriction enzymes with novel specificities (Kong et al. *Nucl. Acids Res.* 28;3216–3223 (2000)). Thus microbial genome mining has emerged as a new way of screening and cloning new type II restriction enzymes and methylases and their isoschizomers.

Because purified restriction endonucleases and modification methylases are useful tools for creating recombinant molecules in the laboratory, there is a strong commercial interest to obtain bacterial strains through recombinant DNA techniques that produce large quantities of restriction enzymes and methylases. Such over-expression strains should also simplify the enzyme purification process.

SUMMARY OF THE INVENTION

The present invention relates to a method for cloning BsrGI restriction endonuclease gene (bsrGIR) from *Bacillus stearothermophilus* GR75 into *E. coli* by inverse PCR and direct PCR from genomic DNA using primers that were based on the DNA sequences obtained via methylase selection.

The bsrGIM gene was cloned from a mixture of seven DNA libraries by the methylase selection. The methylase gene and its adjacent DNA were sequenced by primer walking of the original methylase positive clone and its subclones. A truncated ORF of 309 bp was found upstream of the bsrGIM gene. Since R-M genes in a restriction and modification system are usually located in close proximity to each other, efforts were made to clone the upstream ORF by inverse PCR and direct PCR. Following two rounds of inverse PCR, one 1170-bp ORF was found upstream of the methylase gene. Two small ORFs were also identified downstream of the methylase gene. The 1170-bp ORF was amplified by PCR and cloned in a T7 expression vector pACYC-T7ter. BsrGI restriction endonuclease was detected in IPTG-induced cell extract. The final recombinant BsrGI expression strain was *E. coli* ER2566 [pUC-BsrGIM, pACYC-T7ter-BsrGIR].

BRIEF DESCRIPTION OF THE DRAWINGS

FIG. 2. BsrGI methylase gene sequence (bsrGIM, 1947 bp) (SEQ ID NO:1) and the encoded amino acid sequence (SEQ ID NO:2).

FIG. 3. BsrGI endonuclease gene sequence (bsrGIR, 1170 bp) (SEQ ID NO:3) and the encoded amino acid sequence (SEQ ID NO:4).

DETAILED DESCRIPTION OF THE INVENTION

Figure 1:
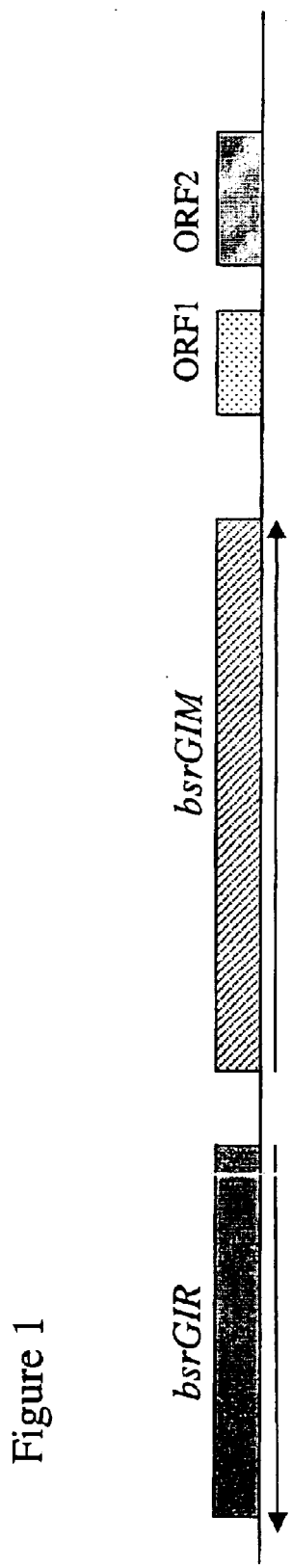
FIG. 1. Gene organization of BsrGI R-M system, bsrGIR, BsrGI restriction endonuclease gene; bsrGIM, BsrGI methylase gene.

The method described herein by which the bsrGIM and bsrGIR genes are preferably cloned and expressed in *E. coli* include the following steps:

1. Preparation of Genomic DNA, Restriction Digestion, and Construction of Genomic DNA Library Genomic DNA was prepared from *Bacillus stearothermophilus* GR75 (BsrGI-producing strain) and digested with BamHI, HindIII, PstI, SacI, SalI, SphI, and XbaI, respectively. A pUC19-derived cloning vector (pUC-Cm) was constructed to include the $Cm^R$ gene that was flanked by two BsrGI sites. The original cloning vector pUC19 does not contain any BsrGI site. Our experience has shown that simply introducing a cut site into cloning vectors provides a high background and, in general is not an efficient selection tool. The introduction of $Cm^R$ gene flanked by two BsrGI provided more powerful selection for the M.BsrGI⁺ clones. The cloning vector pUC-Cm was digested with BamHI, HindIII, PstI, SacI, SalI, SphI, and XbaI, respectively. After CIP treatment of the vector the genomic DNA was ligated to the vector with compatible ends. The ligated DNA was used to transform cells by electroporation. Approximately 4,000 $Ap^R$ transformants were obtained for each library. The cells from seven libraries were pooled together and amplified. Plasmid DNA was prepared, generating a mixed plasmid library.

2. Cloning of bsrGIM Gene by Methylase Selection

The mixed primary plasmid library DNA was challenged with BsrGI endonuclease. The digested DNA was transferred into ER1992 by transformation, producing ~500 $Ap^R$ $Cm^R$ survivors. Plasmid DNA was prepared from cultures of 72 transformants. One BsrGI resistant clone was identified following BsrGI digestion and gel electrophoresis.

3. Restriction Mapping and Subcloning of the Insert

The plasmid DNA from BsrGI resistant clone was digested with restriction enzymes AflIII, BamHI, BsaXI, HincII, HindIII, KasI, KpnI, NdeI, PstI, SacI, SalI, SapI, SphI, StuI, and XbaI to estimate the insert size. The insert was determined to be approximately 11 kb which was derived from the XbaI library. To facilitate the sequencing of the insert, seven HincII fragments from the 11 kb insert were subcloned into pUC19.

4. Construction of bsrGIM Gene Deletion Clones

The original methylase positive plasmid was digested with KpnI, NdeI, and SphI, respectively. The plasmid DNA was self-ligated in low DNA concentration to promote deletion. The deletion subclones, ~3.5 kb KpnI fragment deletion, ~9.5 kb NdeI fragment deletion, ~1.2 kb SphI fragment deletion, were all cleaved by BsrGI, indicating that the deleted DNA removed part of or all of the bsrGIM gene. It demonstrated the resistance to BsrGI digestion was conferred by the gene product within the 11 kb insert.

5. DNA Sequence Analysis of the bsrGIM Gene

The HincII subclones were sequenced by pUC universal forward and reverse primers. One amino acid sequence translated from the DNA sequence indicated conserved amino-methyltransferase motifs. The methylase gene was sequenced by primer walking from the HincII subclone and the original methylase positive clone. The bsrGIM gene was found to be 1947 bp, encoding a protein of 76.2 kDa.

6. Inverse PCR Amplification of DNA Upstream of BsrGI Methylase

After identification of the bsrGIM gene, efforts were made to clone adjacent DNA. Two small ORFs (306 bp and 399 bp) were found downstream of the bsrGIM gene, but these two ORFs are too small to encode an endonuclease. Thus, inverse PCR efforts were concentrated on the upstream of the M gene, where a truncated ORF of 309 bp was located.

The genomic DNA was digested with restriction enzymes, purified, and self-ligated. The circular DNA molecules were used as templates for inverse PCR. PCR products were found in the ApoI, DraI, PacI, RsaI, and TaqI templates. The PCR products were purified and sequenced. It generated about 600 bp of new sequence. A second round of inverse PCR was carried out from which a ~800 bp PCR product was found in the HaeIII-derived template. The PCR product was purified and sequenced, which provide another ~400 bp of new sequence. A stop codon was found in the finished ORF with 1170 bp, encoding a protein with molecular mass of 44.7 kDa.

7. Expression of bsrGIR Gene in *E. coli*

The successful expression strategy was to express bsrGIM gene in a high-copy-number plasmid pUC and the bsrGIR gene in a low-copy-number T7 vector pACYC-T7ter.

Figure 5:
FIG. 5. Recombinant BsrGI endonuclease activity in cell extract. A DNA was used as the substrate. Lanes 1, DNA size marker; Lanes 2 and 6, λ DNA digested with native BsrGI; Lanes 3–5, ⅛, ⅟₁₆, ⅟₃₂, diluted cell extract added in the restriction digestions; Lane 7, λ DNA.

The plasmid pUC-Cm-BsrGIM was the original methylase positive clone isolated from the methylase selection. The $Cm^R$ gene was deleted to make plasmid pUC-BsrGIM, which was transferred into ER2566 to premodify *E. coli* host. The bsrGIR gene was amplified from genomic DNA by PCR with Vent® DNA polymerase. Following purification and digestion with NdeI and BamHI, it was ligated to CIP-treated pACYC-T7ter ($Cm^R$) with compatible ends. The ligated DNA was transferred into pre-modified host ER2566 [pUC-BsrGIM] by transformation. Ten ml of cell cultures were made from four individual transformants and target protein production induced with IPTG. Cell extracts were prepared and assayed for BsrGI endonuclease activity on λ DNA substrate. Two active BsrGI-producing clones were found in IPTG-Induced cell extracts. The BsrGI activity of one active clone was shown in FIG. 5.

The plasmid DNA pACYC-T7ter-BsrGIR clone was prepared by Qiagen (Germantown, Md.) column and the entire insert was sequenced. It was found that the insert contained the wild type coding sequence.

The Example is given to illustrate embodiments of the present invention as its presently preferred to practice. It will be understood that the Example is illustrative and that is not considered as restricted thereto except as indicated in the appended claims.

The references cited above and below are herein incorporated by reference.

EXAMPLE 1

Cloning of BsrGI Restriction-Modification System in *E. coli*

1. Preparation of Genomic DNA

Genomic DNA was prepared from 5 g of *Bacillus stearothermophilus* GR75 (NEB#813, New England Biolabs strain collection, New England Biolabs, Inc., Beverly, Mass.) by the standard procedure consisting of the following steps:

a. Cell lysis by addition of lysozyme (2 mg/ml final), sucrose (1% final), and 50 mM Tris-HCl, pH 8.0.
 b. Further cell lysis by addition of SDS at a final concentration of 0.1%.
 c. Further cell lysis by addition of 1% Triton X-100, 62 mM EDTA, 50 mM Tris-HCl, pH 8.0.
 d. Removal of proteins by phenol-$CHCl_3$ extraction of DNA 3 times (equal volume) and $CHCl_3$ extraction once.
 e. Dialysis in 4 liters of TE buffer, buffer change twice.
 f. RNase A treatment at 37° C. for 1 h to remove RNA.
 g. Genomic DNA precipitation in 95% ethanol, centrifuged, washed, dried and resuspended in TE buffer.

2. Restriction Digestion of Genomic DNA and Construction of Genomic DNA Library

The genomic DNA was digested completely with BamHI, HindIII, PstI, SacI, SalI, SphI, and XbaI, respectively at 37° C. for 1 h. A pUC19-derived cloning vector (pUC-Cm) was constructed to contain the $Cm^R$ gene that was flanked by two BsrGI sites. The original cloning vector pUC19 does not contain any BsrGI site for M.BsrGI methylase selection. The introduction of $Cm^R$ gene flanked by two BsrGI provided more powerful selection for the M.BsrGI$^+$ clones. The cloning vector pUC-Cm was also digested with BamHI, HindIII, PstI, SacI, SalI, SphI, and XbaI, respectively at 37° C. for 2 h. The linearized DNA was then treated with 10 units of CIP at 37° C. for 1 h. CIP was removed by heat-inactivation and the DNA further purified by running through a Qiagen (Germantown, Md.) spin column. Genomic DNA was ligated to the vector with compatible ends at 16° C. overnight using T4 DNA ligase. The ligated DNA was used to transform cells by electroporation and transformed cells plated on Ap plates (100 µg/ml). Approximately 4,000 $Ap^R$ transformants were obtained from each library. The cells from seven libraries were mixed together and amplified in 1 L LB plus Ap. Plasmid DNA was prepared by Qiagen (Germantown, Md.) Maxi column, generating a mixed plasmid library.

2. Cloning of bsrGIM Gene by Methylase Selection

The primary plasmid DNA (1 µg, 2 µg, 3 µg, 4 µg and 5 µg DNA, respectively) was challenged with 50 units of BsrGI digestion at 60° C. for 4 h. The challenged DNA was transferred into *E. coli* ER1992 by transformation, generating ~500 $AP^R$ survivors. The standard transformation procedure was described as follows. 10–50 ng of digested plasmid DNA were mixed with 100 µl of chemical competent cells and incubated at 4° C. for 30 min. The cell-DNA mixture was heat-treated at 37° C. for 5 min. Equal volume of SOB or LB was added to the cell mixture and amplification was carried out at 37° C. for 1 h. Cells were plated on Ap (100 µg) plus Cm (33 µg) plates and incubated at 37° C. incubator overnight. $Ap^R$ and $Cm^R$ double selection greatly reduced the number of survivor transformants. 72 plasmid DNAs were prepared by Qiagen (Germantown, Md.) spin columns from 1.5 ml overnight cell cultures. After digestion with BsrGI and gel electrophoresis, one true resistant clone was found (#23).

3. Restriction Mapping and Subcloning of the Insert

The BsrGI resistant clone #23 was digested with restriction enzymes AflIII, BamHI, HincII, HindIII, KasI, KpnI, NdeI, PstI, SacI, SalI, SapI, SphI, StuI, and XbaI, respectively to estimate the insert size. The insert was determined to be approximately 11 kb which was derived from the XbaI genomic DNA library. To facilitate the sequencing of the insert, seven HincII fragments in the range of 600 bp–2300 bp were subcloned into pUC19.

4. Construction of bsrGIM Gene Deletion Clones

To confirm the resistance is due to methylation of BsrGI site by the cloned methylase and not due to the deletion of BsrGI sites in the vector, the original methylase positive plasmid was digested with KpnI, NdeI, and SphI, respectively. The plasmid DNA was self-ligated in low DNA concentration to promote deletion. The deletion subclones, ~3.5 kb KpnI fragment deletion, ~9.5 kb NdeI fragment deletion, ~1.2 kb SphI fragment deletion, were all cleaved by BsrGI, indicating that the deleted DNA removed part of or all of the bsrGIM gene. It demonstrated the resistance to BsrGI digestion was conferred by the 11 kb insert, in which the bsrGIM gene was located.

5. DNA Sequence Analysis of the bsrGIM Gene

HincII-fragment subclones were sequenced by the dideoxy terminator method using AmpliTaq (Torrence, Calif.) dideoxy terminator sequencing kit and an ABI 373A sequencing machine with pUC universal forward and reverse primers. One amino acid sequence translated from the DNA sequence indicated conserved amino-methyltransferase motifs. The bsrGIM methylase gene was sequenced by primer walking from the HincII-subclones and the original methylase positive clone. The bsrGIM gene was found to be 1947 bp, encoding a protein of 76.2 kDa. M.BsrGI is predicted to be an amino-methyltransferase (N4C methylase or N6A methylase) based on the amino acid sequence homology with other methylases. The sequencing primers used in the primer walking were listed below:

5' ACTCTGCAATGGCAGCCATTATGTTA 3' 287-042 (SEQ ID NO:5)

5' ACATTCTCGGCTATGTTGGCTCTC 3' 287-043 (SEQ ID NO:6)

5' ACTGAAAATGGAGMGTCGATGTG 3' 287-044 (SEQ ID NO:7)

5' TATGCAATACAGACATACTTTAGC 3' 287-045 (SEQ ID NO:8)

5' ACTAGATAGAGTCGATATTATAATAGG 3' 287-107 (SEQ ID NO:9)

5' GAACCACATGTTGGGTCTAAATAAG 3' 287-108 (SEQ ID NO:10)

5' CACATTCTCGGCTATGTTGGCTCTCTC 3' 287-265 (SEQ ID NO:11)

5' AGAAGCTTATAAACTAGATAGAGTCG 3' 287-266 (SEQ ID NO:12)

5' GGCAGAAGTGATTGAGTTTTATTC 3' 287-267 (SEQ ID NO:13)

5' AAGCTTATAAACTAGATAGAGTCG 3' 287-313 (SEQ ID NO:14)

5' AATCCACCTTGGGTTAACTGGGAGTAC 3' 287-314 (SEQ ID NO:15)

5' CATTTATAAGGCGAGAACAGGTGT 3' 287-375 (SEQ ID NO:16)

5' CACTGGGGGTGCGAACGCTGTATAC 3' 287-376 (SEQ ID NO:17)

5' GTGTGGAGATATATTGCAACTGAG 3' 288-102 (SEQ ID NO:18)

5' AGTGATGTATATTAGCATGGATGA 3' 288-103 (SEQ ID NO:19)

6. Inverse PCR Amplification of DNA Upstream of BsrGI Methylase

After identification of the bsrGIM gene, efforts were made to clone adjacent DNA. Two small ORFs of 306 bp and 399 bp were found downstream of the bsrGIM gene, but these two ORFs are too small to encode an endonuclease although it was not ruled out that they may encode a protein with two heterodimeric subunits. It was demonstrated below that the bsrGIR gene is located upstream of the M gene and the downstream 306 bp and 399 bp ORFs are not bsrGIR gene.

Inverse PCR efforts were concentrated on the upstream region of the bsrGIM gene, where a truncated ORF of 309 bp was located. Two inverse PCR primers were synthesized with the following sequence:

5' TCAAGGTAAAGCCTCTTGTCAGAG 3' 287-315. (SEQ ID NO:20)

5' ATAGAGCTACCACAGATAATGGTG 3' 287-316. (SEQ ID NO:21)

The Bst genomic DNA was digested with restriction enzymes ApoI, DraI, HindIII, HpyCH4V, MfeI, PacI, RsaI, SphI, TaqI, and XmnI, respectively at the desired temperatures (ApoI digestion at 50° C., TaqI digestion at 65° C., the remaining digestion at 37° C.). The digested DNA was purified through Qiagen (Germantown, Md.) spin columns. Self-ligation was set up at a low DNA concentration at 2 µg/ml overnight at 16° C. T4 DNA ligase was inactivated at 65° C. for 30 min and the circular DNA was precipitated in ethanol and used as the template for inverse PCR. PCR conditions were 94° C. for 2 min, 1 cycle; 94° C. for 30 sec, 55° C. for 30 sec, 72° C. for 2 min for 35 cycles. PCR products were found in the ApoI, DraI, PacI, RsaI, and TaqI templates. The PCR products were purified from a low-melting agarose gel, treated with β-agarase for 2 h, precipitated with ethanol, and sequenced directly with primers 287-315 and 316. The first round of inverse PCR generated about 600 bp of new sequence.

In a second round of inverse PCR, two primers were made with the following sequence:

5' GGGTTCTCACAAAAACCTACTCCA 3' 288-74 (SEQ ID NO:22)

5' GGTACAATAGTCAAAATGATAGATG 3' 288-75 (SEQ ID NO:23)

The Bst genomic DNA was digested with restriction enzymes AgeI, AluI, ApoI, BsaWI, BsrFI, HaeIII, HincII, HpaII, MfeI PacI, SpeI, SspI, TaqI, and XbaI, respectively at the desired temperatures (ApoI digestion at 50° C., BsaWI digestion at 60° C., TaqI digestion at 65° C., the remaining digestion at 37° C.). The digested DNA was purified through Qiagen (Germantown) spin columns. Self-ligation was set up at a low DNA concentration at 2 µg/ml overnight at 16° C. T4 DNA ligase was inactivated at 65° C. for 30 min and the circular DNA was precipitated in ethanol and used as the template for inverse PCR. PCR conditions were 94° C. for 2 min, 1 cycle; 94° C. for 30 sec, 55° C. for 30 sec, 72° C. for 2 min for 35 cycles. An 800 bp PCR product was found in the HaeIII template. The PCR product was purified from a low-melting agarose gel, treated with β-agarase for 2 h, precipitated with ethanol, and sequenced directly with primers 288-74 and 75, which provided another ~400 bp of new sequence. A stop codon was found in the finished bsrGIM gene of 1170 bp, encoding a protein with molecular mass of 44.7 kDa.

7. Expression of bsrGIR Gene in *E. coli*

The successful expression strategy was co-expression of bsrGIM gene in a high-copy-number plasmid pUC and the bsrGIR gene in a low-copy-number T7 vector pACYC-T7ter.

The plasmid pUC-Cm-BsrGIM was the original methylase positive clone isolated from the methylase selection. The Cm$^R$ gene was deleted to make plasmid pUC-BsrGIM, which was transferred into ER2566 to pre-modify *E. coli* host by standard transformation.

Figure 4:
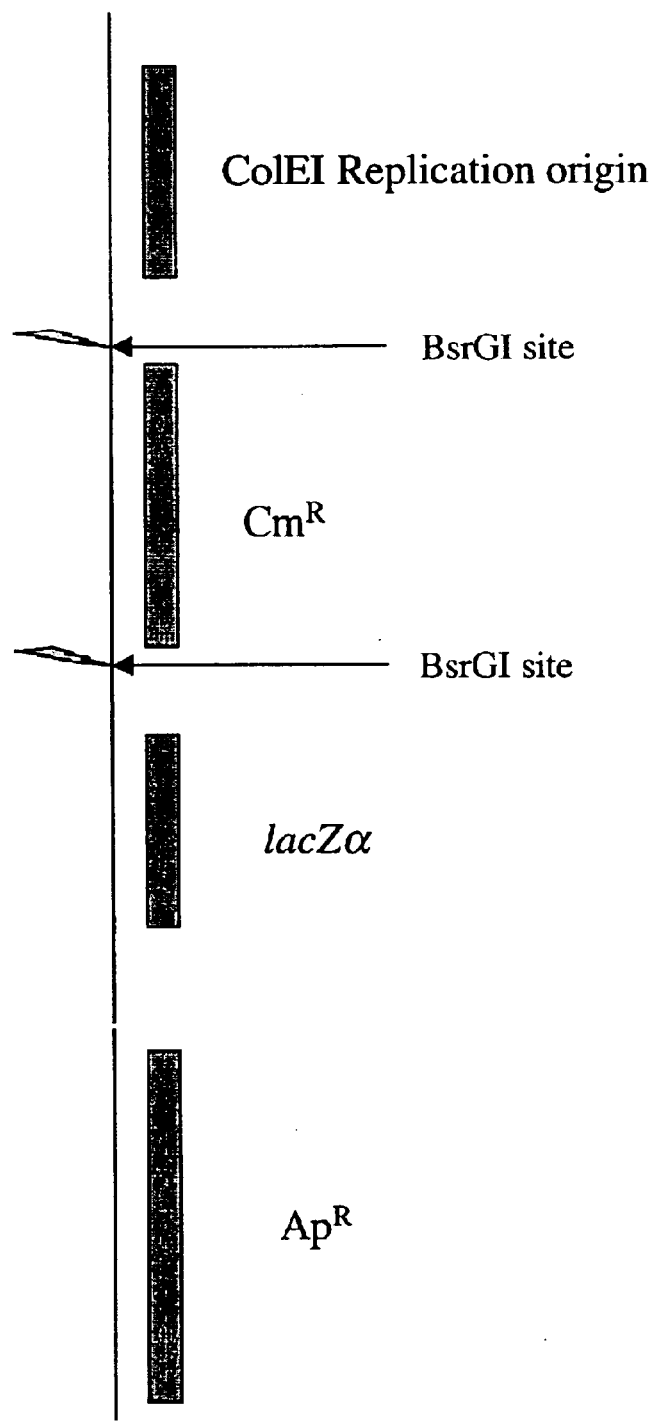
FIG. 4. Schematic diagram of cloning vector pUC-Cm. $Cm^R$, Chloramphenicol resistance gene flanked by BsrGI sites. $Ap^R$, ampicillin resistance gene (β-lactamase), lacZα, β-galactosidase gene α fragment. MCS, multiple cloning sites.

The 1170-bp bsrGIR gene was amplified from genomic DNA by PCR with Vent DNA polymerase. The PCR primers have the following sequences. The forward and the reverse primers contain NdeI site and BamHI site, respectively. PCR conditions were 94° C. for 2 min, 1 cycle; 94° C. for 30 sec, 55° C. for 30 sec, 72° C. for 3 min for 20 cycles. Following purification through Qiagen (Germantown, Md.) spin columns and digestion with NdeI and BamHI overnight at 37° C., the PCR DNA was purified again by passing through Qiagen (Germantown, Md.) spin columns. It was then ligated to CIP-treated pACYC-T7ter (Cm$^R$) with compatible ends (ligation condition: ~100 ng vector, ~500 ng PCR insert, 2 µl 10× ligation buffer, 1 µl T4 DNA ligase (400 units), in a total volume of 20 µl at 16° C. overnight). The ligated DNA was transferred into pre-modified host ER2566 [pUC-BsrGIM] by transformation. ER2566 [pUC-BsrGIM] competent cells were made competent by CaCl$_2$ treatment of the exponential phase cells at 4° C. for 30 min. Ten ml of cell cultures were made from four individual transformants and target protein production induced with IPTG. Cell extracts were prepared and assayed for BsrGI endonuclease activity on 1 DNA substrate. Two active BsrGI-producing clones were found in IPTG-induced cell extracts. The BsrGI activity of one active clone (#4) was shown in FIG. 4. The plasmid DNA pACYC-T7ter-BsrGIR was prepared by Qiagen (Germantown, Md.) column and the entire insert was sequenced. It was confirmed that the insert contained the wild type coding sequence.

8. Thermostability of the Recombinant BsrGI Endonuclease

Cell extracts containing recombinant BsrGI were heated at 50° C. and 60° C., respectively, for 30 min. Heat-denatured *E. coli* proteins were removed by centrifugation at 14 K rpm for 15 min. The clarified lysates were used to digest λ DNA at 37° C. It was found that pre-treatment at 50° C. did not alter cleavage activity. However, heat-treatment at 60° C. reduced BsrGI cleavage activity ~94%. It is concluded that restriction digestion using recombinant BsrGI can be carried out at 37° C. to 50° C. BsrGI is a thermostable restriction endonuclease.

The strain NEB#1502, ER2566 [pUC-BsrGIM, pACYC-T7ter-BsrGIR] has been deposited under the terms and conditions of the Budapest Treaty with the American Type Culture Collection on 08 Jan. 2003 and received ATCC Accession No. PTA 4892.

What is claimed is:

1. Isolated DNA encoding the BsrGI restriction endonuclease, wherein the isolated DNA is obtainable from *Bacillus stearothermophilus* GR75.

2. A recombinant DNA vector comprising a vector into which a DNA segment encoding the BsrGI restriction endonuclease has been inserted.

3. Isolated DNA encoding the BsrGI restriction endonuclease and BsrGI methylase, wherein the isolated DNA is obtainable from ATCC No. PTA-4892.

4. A vector which comprise the isolated DNA of claim 3.

5. A host cell transformed by the vector of claims 2 or 4.

6. A method of producing recombinant BsrGI restriction endonuclease comprising culturing a host cell transformed with the vector of claims 2 or 4 under conditions suitable for expression of said endonuclease and methylase.

* * * * *

UNITED STATES PATENT AND TRADEMARK OFFICE
CERTIFICATE OF CORRECTION

PATENT NO.         : 6,869,786 B1                                      Page 1 of 1
APPLICATION NO.    : 10/338898
DATED              : March 22, 2005
INVENTOR(S)        : Shuang-Yong Xu It is certified that error appears in the above-identified patent and that said Letters Patent is hereby corrected as shown below:

At column 2, line 34, delete "Therlault" and insert -- Theriault --, therefor.

At column 3, line 23, delete "28;3216-3223" and insert -- 28:3216-3223 --, therefor.

At column 4, line 10, delete "A" and insert -- $\lambda$ --, therefor.

At column 4, line 52, delete "Sad" and insert -- Sacl --, therefor.

At column 9, line 20, delete "1" and insert -- $\lambda$ --, therefor.

Signed and Sealed this
Seventeenth Day of May, 2011

David J. Kappos
*Director of the United States Patent and Trademark Office*

SEQUENCE LISTING

<160> NUMBER OF SEQ ID NOS: 23

<210> SEQ ID NO 1
<211> LENGTH: 1947
<212> TYPE: DNA
<213> ORGANISM: Bacillus stearothermophilus GR75
<220> FEATURE:
<221> NAME/KEY: CDS
<222> LOCATION: (1)..(1947)
<223> OTHER INFORMATION:

<400> SEQUENCE: 1

```
atg att gat tta aat aaa gtt aga att tct ctt caa gac gag aag tct        48
Met Ile Asp Leu Asn Lys Val Arg Ile Ser Leu Gln Asp Glu Lys Ser
1               5                   10                  15 aat ctt tct aaa atg tct aag gaa ttg att cat att ttc tat tta agg        96
Asn Leu Ser Lys Met Ser Lys Glu Leu Ile His Ile Phe Tyr Leu Arg
            20                  25                  30 ctt cta aac ccg caa gaa agt tta aag caa ata aag gac aat tgg gaa       144
Leu Leu Asn Pro Gln Glu Ser Leu Lys Gln Ile Lys Asp Asn Trp Glu
        35                  40                  45 aaa gaa ttt aat ttt ata tat ggc gat ata aaa aat aat ttt tcg agc       192
Lys Glu Phe Asn Phe Ile Tyr Gly Asp Ile Lys Asn Asn Phe Ser Ser
    50                  55                  60 aat aaa aag gta aaa ccg caa gaa ttg gca aat act tat tca atc aat       240
Asn Lys Lys Val Lys Pro Gln Glu Leu Ala Asn Thr Tyr Ser Ile Asn
65                  70                  75                  80 act gaa aat gga gaa gtc gat gtg ttt tgt ctg ttt tat gca ata cag       288
Thr Glu Asn Gly Glu Val Asp Val Phe Cys Leu Phe Tyr Ala Ile Gln
                85                  90                  95 aca tac ttt agc tta ttt ata aaa tta cta acc tac aaa cta tta agc       336
Thr Tyr Phe Ser Leu Phe Ile Lys Leu Leu Thr Tyr Lys Leu Leu Ser
            100                 105                 110 ggt atc aaa gaa gat aaa gta agt ttc gaa aat tac aat ttt agg gag       384
Gly Ile Lys Glu Asp Lys Val Ser Phe Glu Asn Tyr Asn Phe Arg Glu
        115                 120                 125 ttt ata gtt tct att tta cat ggc agt tat ttt gag aat cta ggg att       432
Phe Ile Val Ser Ile Leu His Gly Ser Tyr Phe Glu Asn Leu Gly Ile
    130                 135                 140
```

-continued

| | |
|---|---|
| gaa aac tac tgt tat aca gat tgg ttt tgt tgg ata gat gaa tgt tta<br>Glu Asn Tyr Cys Tyr Thr Asp Trp Phe Cys Trp Ile Asp Glu Cys Leu<br>145                    150                    155                    160 | 480 |
| gac aat gaa ata gag agt aaa att ttt aat tta tta cag gaa tta aac<br>Asp Asn Glu Ile Glu Ser Lys Ile Phe Asn Leu Leu Gln Glu Leu Asn<br>                    165                    170                    175 | 528 |
| aaa ttt gat gag att aat aac tta cag gaa ttt att tca att cac aat<br>Lys Phe Asp Glu Ile Asn Asn Leu Gln Glu Phe Ile Ser Ile His Asn<br>                180                    185                    190 | 576 |
| aac gat aat atc aaa caa atg tat gaa att att ata cct cgc caa tta<br>Asn Asp Asn Ile Lys Gln Met Tyr Glu Ile Ile Ile Pro Arg Gln Leu<br>                195                    200                    205 | 624 |
| agg cat gct ctt ggt gaa tac tat act ccc gat tgg tta gca ttg tat<br>Arg His Ala Leu Gly Glu Tyr Tyr Thr Pro Asp Trp Leu Ala Leu Tyr<br>210                    215                    220 | 672 |
| act ata gaa aat gta ata gaa tta agt aaa aaa gaa gtt gag gag ttt<br>Thr Ile Glu Asn Val Ile Glu Leu Ser Lys Lys Glu Val Glu Glu Phe<br>225                    230                    235                    240 | 720 |
| aac aaa act tat tta gac cca aca tgt ggt tct ggt aca ttt tta ttt<br>Asn Lys Thr Tyr Leu Asp Pro Thr Cys Gly Ser Gly Thr Phe Leu Phe<br>                    245                    250                    255 | 768 |
| aaa aca ata caa cgt tta aga aaa agt gat ata aaa ttg aat aag att<br>Lys Thr Ile Gln Arg Leu Arg Lys Ser Asp Ile Lys Leu Asn Lys Ile<br>                260                    265                    270 | 816 |
| ata tat tca gta agg gga ttt gat gta aat cca ata gca gta tta act<br>Ile Tyr Ser Val Arg Gly Phe Asp Val Asn Pro Ile Ala Val Leu Thr<br>275                    280                    285 | 864 |
| gct aag act aac tat tta ata tca ata att gat tta ata aaa gat aag<br>Ala Lys Thr Asn Tyr Leu Ile Ser Ile Ile Asp Leu Ile Lys Asp Lys<br>290                    295                    300 | 912 |
| acc gta ata aat tta cct gtt tat aac tat gat gta att aat tca cca<br>Thr Val Ile Asn Leu Pro Val Tyr Asn Tyr Asp Val Ile Asn Ser Pro<br>305                    310                    315                    320 | 960 |
| ata tta aaa gaa aat aaa ctt ctt tct gtt gat ata aat aat gtt att<br>Ile Leu Lys Glu Asn Lys Leu Leu Ser Val Asp Ile Asn Asn Val Ile<br>                    325                    330                    335 | 1008 |
| tac aat att ccg tta tca att tta aag gat gag cat ttt aaa acc ttt<br>Tyr Asn Ile Pro Leu Ser Ile Leu Lys Asp Glu His Phe Lys Thr Phe<br>                340                    345                    350 | 1056 |
| aaa aaa ata tta ata caa tca tta aaa agt aac ttg aat cct gaa gag<br>Lys Lys Ile Leu Ile Gln Ser Leu Lys Ser Asn Leu Asn Pro Glu Glu<br>355                    360                    365 | 1104 |
| ttt tat aac ctt ctt ttg gaa caa aaa ata aat cta aaa aat aag gca<br>Phe Tyr Asn Leu Leu Leu Glu Gln Lys Ile Asn Leu Lys Asn Lys Ala<br>370                    375                    380 | 1152 |
| gaa gtg att gag ttt tat tct aaa ctt cta aat agt aca aat ata aaa<br>Glu Val Ile Glu Phe Tyr Ser Lys Leu Leu Asn Ser Thr Asn Ile Lys<br>385                    390                    395                    400 | 1200 |
| ata cga cta ata att gct tat tta tta att aat cgt tta gaa gct tat<br>Ile Arg Leu Ile Ile Ala Tyr Leu Leu Ile Asn Arg Leu Glu Ala Tyr<br>                    405                    410                    415 | 1248 |
| aaa cta gat aga gtc gat att ata ata gga aat cca cct tgg gtt aac<br>Lys Leu Asp Arg Val Asp Ile Ile Ile Gly Asn Pro Pro Trp Val Asn<br>                420                    425                    430 | 1296 |
| tgg gag tac ctt cct aag gag tat aga gaa aaa tct caa cac ctc tgg<br>Trp Glu Tyr Leu Pro Lys Glu Tyr Arg Glu Lys Ser Gln His Leu Trp<br>                    435                    440                    445 | 1344 |
| gta gaa tat ggt ctt ttt gct atg aag ggg aga gat tta agt ttc tcg<br>Val Glu Tyr Gly Leu Phe Ala Met Lys Gly Arg Asp Leu Ser Phe Ser<br>450                    455                    460 | 1392 |

```
aaa gaa gat att tca att ctt ata act tat tta gtt att gat aaa ttt        1440
Lys Glu Asp Ile Ser Ile Leu Ile Thr Tyr Leu Val Ile Asp Lys Phe
465                 470                 475                 480 ctc aaa gat tat gga cat tta gca ttt gtt ata aga caa ggt att ttc        1488
Leu Lys Asp Tyr Gly His Leu Ala Phe Val Ile Arg Gln Gly Ile Phe
                485                 490                 495 aaa tct gca aaa aac ggt ata ggt ttt aga agg ttt caa gtt gga aat        1536
Lys Ser Ala Lys Asn Gly Ile Gly Phe Arg Arg Phe Gln Val Gly Asn
            500                 505                 510 gat tac tat cta aaa gta aaa aga gta gat gac ctc tcc ttc att aaa        1584
Asp Tyr Tyr Leu Lys Val Lys Arg Val Asp Asp Leu Ser Phe Ile Lys
        515                 520                 525 cca ttt gaa aat gca act aat agt aca tct gtg tta ttc tta caa aag        1632
Pro Phe Glu Asn Ala Thr Asn Ser Thr Ser Val Leu Phe Leu Gln Lys
    530                 535                 540 aat cat aaa aca gaa tat cca gtt cca tat tat gtt tgg aaa aaa aga        1680
Asn His Lys Thr Glu Tyr Pro Val Pro Tyr Tyr Val Trp Lys Lys Arg
545                 550                 555                 560 aat tcc gtt tct aaa tta act tta aga aca tat gat gag ttg tca gat        1728
Asn Ser Val Ser Lys Leu Thr Leu Arg Thr Tyr Asp Glu Leu Ser Asp
                565                 570                 575 ata cta aca aac gta gat ata aaa gaa atg ata gca ttt cct tct gat        1776
Ile Leu Thr Asn Val Asp Ile Lys Glu Met Ile Ala Phe Pro Ser Asp
            580                 585                 590 aaa aat gat gag aca tcc tta tgg ata aca ata cca gag aaa aca ctt        1824
Lys Asn Asp Glu Thr Ser Leu Trp Ile Thr Ile Pro Glu Lys Thr Leu
        595                 600                 605 tct gtg att acc aat gta cta ggt aca aac agt tat aag gcg aga aca        1872
Ser Val Ile Thr Asn Val Leu Gly Thr Asn Ser Tyr Lys Ala Arg Thr
    610                 615                 620 ggt gtt ttc act ggg ggt gcg aac gct gta tac tgg ttg gaa att aaa        1920
Gly Val Phe Thr Gly Gly Ala Asn Ala Val Tyr Trp Leu Glu Ile Lys
625                 630                 635                 640 gat aaa aag aca atg gta aaa tac tag                                    1947
Asp Lys Lys Thr Met Val Lys Tyr
                645

<210> SEQ ID NO 2
<211> LENGTH: 648
<212> TYPE: PRT
<213> ORGANISM: Bacillus stearothermophilus GR75

<400> SEQUENCE: 2

Met Ile Asp Leu Asn Lys Val Arg Ile Ser Leu Gln Asp Glu Lys Ser
1               5                   10                  15

Asn Leu Ser Lys Met Ser Lys Glu Leu Ile His Ile Phe Tyr Leu Arg
            20                  25                  30

Leu Leu Asn Pro Gln Glu Ser Leu Lys Gln Ile Lys Asp Asn Trp Glu
        35                  40                  45

Lys Glu Phe Asn Phe Ile Tyr Gly Asp Ile Lys Asn Asn Phe Ser Ser
    50                  55                  60

Asn Lys Lys Val Lys Pro Gln Glu Leu Ala Asn Thr Tyr Ser Ile Asn
65                  70                  75                  80

Thr Glu Asn Gly Glu Val Asp Val Phe Cys Leu Phe Ala Ile Gln
                85                  90                  95

Thr Tyr Phe Ser Leu Phe Ile Lys Leu Leu Thr Tyr Lys Leu Leu Ser
                100                 105                 110

Gly Ile Lys Glu Asp Lys Val Ser Phe Glu Asn Tyr Asn Phe Arg Glu
```

-continued

```
            115                 120                 125
Phe Ile Val Ser Ile Leu His Gly Ser Tyr Phe Glu Asn Leu Gly Ile
130                 135                 140
Glu Asn Tyr Cys Tyr Thr Asp Trp Phe Cys Trp Ile Asp Glu Cys Leu
145                 150                 155                 160
Asp Asn Glu Ile Glu Ser Lys Ile Phe Asn Leu Leu Gln Glu Leu Asn
                    165                 170                 175
Lys Phe Asp Glu Ile Asn Asn Leu Gln Glu Phe Ile Ser Ile His Asn
                    180                 185                 190
Asn Asp Asn Ile Lys Gln Met Tyr Glu Ile Ile Pro Arg Gln Leu
                195                 200                 205
Arg His Ala Leu Gly Glu Tyr Tyr Thr Pro Asp Trp Leu Ala Leu Tyr
210                 215                 220
Thr Ile Glu Asn Val Ile Glu Leu Ser Lys Lys Glu Val Glu Glu Phe
225                 230                 235                 240
Asn Lys Thr Tyr Leu Asp Pro Thr Cys Gly Ser Gly Thr Phe Leu Phe
                    245                 250                 255
Lys Thr Ile Gln Arg Leu Arg Lys Ser Asp Ile Lys Leu Asn Lys Ile
                260                 265                 270
Ile Tyr Ser Val Arg Gly Phe Asp Val Asn Pro Ile Ala Val Leu Thr
            275                 280                 285
Ala Lys Thr Asn Tyr Leu Ile Ser Ile Ile Asp Leu Ile Lys Asp Lys
290                 295                 300
Thr Val Ile Asn Leu Pro Val Tyr Asn Tyr Asp Val Ile Asn Ser Pro
305                 310                 315                 320
Ile Leu Lys Glu Asn Lys Leu Leu Ser Val Asp Ile Asn Asn Val Ile
                    325                 330                 335
Tyr Asn Ile Pro Leu Ser Ile Leu Lys Asp Glu His Phe Lys Thr Phe
                340                 345                 350
Lys Lys Ile Leu Ile Gln Ser Leu Lys Ser Asn Leu Asn Pro Glu Glu
            355                 360                 365
Phe Tyr Asn Leu Leu Leu Glu Gln Lys Ile Asn Leu Lys Asn Lys Ala
    370                 375                 380
Glu Val Ile Glu Phe Tyr Ser Lys Leu Leu Asn Ser Thr Asn Ile Lys
385                 390                 395                 400
Ile Arg Leu Ile Ile Ala Tyr Leu Leu Ile Asn Arg Leu Glu Ala Tyr
                405                 410                 415
Lys Leu Asp Arg Val Asp Ile Ile Ile Gly Asn Pro Pro Trp Val Asn
                420                 425                 430
Trp Glu Tyr Leu Pro Lys Glu Tyr Arg Glu Lys Ser Gln His Leu Trp
            435                 440                 445
Val Glu Tyr Gly Leu Phe Ala Met Lys Gly Arg Asp Leu Ser Phe Ser
    450                 455                 460
Lys Glu Asp Ile Ser Ile Leu Ile Thr Tyr Leu Val Ile Asp Lys Phe
465                 470                 475                 480
Leu Lys Asp Tyr Gly His Leu Ala Phe Val Ile Arg Gln Gly Ile Phe
                485                 490                 495
Lys Ser Ala Lys Asn Gly Ile Gly Phe Arg Arg Phe Gln Val Gly Asn
                500                 505                 510
Asp Tyr Tyr Leu Lys Val Lys Arg Val Asp Asp Leu Ser Phe Ile Lys
            515                 520                 525
Pro Phe Glu Asn Ala Thr Asn Ser Thr Ser Val Leu Phe Leu Gln Lys
530                 535                 540
```

```
Asn His Lys Thr Glu Tyr Pro Val Pro Tyr Tyr Val Trp Lys Lys Arg
545                 550                 555                 560

Asn Ser Val Ser Lys Leu Thr Leu Arg Thr Tyr Asp Glu Leu Ser Asp
                565                 570                 575

Ile Leu Thr Asn Val Asp Ile Lys Glu Met Ile Ala Phe Pro Ser Asp
                580                 585                 590

Lys Asn Asp Glu Thr Ser Leu Trp Ile Thr Ile Pro Glu Lys Thr Leu
                595                 600                 605

Ser Val Ile Thr Asn Val Leu Gly Thr Asn Ser Tyr Lys Ala Arg Thr
                610                 615                 620

Gly Val Phe Thr Gly Gly Ala Asn Ala Val Tyr Trp Leu Glu Ile Lys
625                 630                 635                 640

Asp Lys Lys Thr Met Val Lys Tyr
                645

<210> SEQ ID NO 3
<211> LENGTH: 1170
<212> TYPE: DNA
<213> ORGANISM: Bacillus stearothermophilus GR75
<220> FEATURE:
<221> NAME/KEY: CDS
<222> LOCATION: (1)..(1170)
<223> OTHER INFORMATION:

<400> SEQUENCE: 3 atg aaa aga ata caa gag ttt tgg tat tgt gtt gct tct caa gaa gaa     48
Met Lys Arg Ile Gln Glu Phe Trp Tyr Cys Val Ala Ser Gln Glu Glu
1               5                   10                  15 tta cct ctg tat aag ggg cac gaa att agc tct tct gta tgt gat aat     96
Leu Pro Leu Tyr Lys Gly His Glu Ile Ser Ser Ser Val Cys Asp Asn
                20                  25                  30 ctt ctt gct ttt att gaa cat tat aaa gaa gaa gtt agt aaa ggg aaa    144
Leu Leu Ala Phe Ile Glu His Tyr Lys Glu Glu Val Ser Lys Gly Lys
            35                  40                  45 aac cta aaa acc ttt ctc tca gaa gcc tta att aaa aaa cct tcg att    192
Asn Leu Lys Thr Phe Leu Ser Glu Ala Leu Ile Lys Lys Pro Ser Ile
    50                  55                  60 att aac cat tta agg ttg cta tta gga atc tct gac aag agg ctt tac    240
Ile Asn His Leu Arg Leu Leu Leu Gly Ile Ser Asp Lys Arg Leu Tyr
65                  70                  75                  80 ctt gat tta aca ttc att ttt aat aga gct acc aca gat aat ggt gaa    288
Leu Asp Leu Thr Phe Ile Phe Asn Arg Ala Thr Thr Asp Asn Gly Glu
                85                  90                  95 aga tta tta aat gaa tct aga gaa aat tta gtt aaa cat gat act aaa    336
Arg Leu Leu Asn Glu Ser Arg Glu Asn Leu Val Lys His Asp Thr Lys
                100                 105                 110 ttt ttc att aat caa ctt acc aat tct gat aaa aaa gag cat ttc tct    384
Phe Phe Ile Asn Gln Leu Thr Asn Ser Asp Lys Lys Glu His Phe Ser
            115                 120                 125 cgt tta atc act gat tat ttt att aat aga gga att gaa gat att att    432
Arg Leu Ile Thr Asp Tyr Phe Ile Asn Arg Gly Ile Glu Asp Ile Ile
    130                 135                 140 cac atc ttt tcc aga atg gat aaa aat caa ata act tct att ttt aac    480
His Ile Phe Ser Arg Met Asp Lys Asn Gln Ile Thr Ser Ile Phe Asn
145                 150                 155                 160 aat cta att gct cct aaa gag ata cag caa aaa cag gca aaa tat cgt    528
Asn Leu Ile Ala Pro Lys Glu Ile Gln Gln Lys Gln Ala Lys Tyr Arg
                165                 170                 175 ggt cat ggt gca gaa atg gcc ttc gct aaa ata ttt cat gat tgt ggt    576
```

-continued

```
Gly His Gly Ala Glu Met Ala Phe Ala Lys Ile Phe His Asp Cys Gly
            180                 185                 190 gtt act att gtc cca gaa aat aaa cac atc aat cca atg gca gga tat     624
Val Thr Ile Val Pro Glu Asn Lys His Ile Asn Pro Met Ala Gly Tyr
        195                 200                 205 gac cca aat gta gat ttg act aat atg aca ata gta ccc aga aac gct     672
Asp Pro Asn Val Asp Leu Thr Asn Met Thr Ile Val Pro Arg Asn Ala
    210                 215                 220 gca aat cgg aac att cat agc ttc gat tta gtt gtg aag gat aat gaa     720
Ala Asn Arg Asn Ile His Ser Phe Asp Leu Val Val Lys Asp Asn Glu
225                 230                 235                 240 ggt aat atc aga gta cta gtt caa tcc tta att cac tct tct gac cct     768
Gly Asn Ile Arg Val Leu Val Gln Ser Leu Ile His Ser Ser Asp Pro
                245                 250                 255 ggt cag tat ggc gtt aac aaa tct gat gaa act ctt gaa ata aag aag     816
Gly Gln Tyr Gly Val Asn Lys Ser Asp Glu Thr Leu Glu Ile Lys Lys
            260                 265                 270 tta att aac aat tat aat tca aga aat tca caa aaa ccg gtg tat tta     864
Leu Ile Asn Asn Tyr Asn Ser Arg Asn Ser Gln Lys Pro Val Tyr Leu
        275                 280                 285 cta ggt tca gta gat gga gta ggt ttt tgt gag aac cca aat ggt aca     912
Leu Gly Ser Val Asp Gly Val Gly Phe Cys Glu Asn Pro Asn Gly Thr
    290                 295                 300 ata gtc aaa atg ata gat gtt ttt gat gat ttc ttt caa ata aat act     960
Ile Val Lys Met Ile Asp Val Phe Asp Asp Phe Phe Gln Ile Asn Thr
305                 310                 315                 320 cta ttt aaa atc cca ata ttt ctt caa aaa att ggg tta att gat aat    1008
Leu Phe Lys Ile Pro Ile Phe Leu Gln Lys Ile Gly Leu Ile Asp Asn
                325                 330                 335 gtt aaa gga att aag ttt gat acc gat ttc ttc gat gaa cat gta ata    1056
Val Lys Gly Ile Lys Phe Asp Thr Asp Phe Phe Asp Glu His Val Ile
            340                 345                 350 gaa tac ttt gaa aaa act tat ctt aaa cca gcg aat ata caa aat cta    1104
Glu Tyr Phe Glu Lys Thr Tyr Leu Lys Pro Ala Asn Ile Gln Asn Leu
        355                 360                 365 act aac agt aat tgt aat ttt act aat tat ata aaa gct gga aaa ggt    1152
Thr Asn Ser Asn Cys Asn Phe Thr Asn Tyr Ile Lys Ala Gly Lys Gly
    370                 375                 380 aca gta att ttt aag taa                                            1170
Thr Val Ile Phe Lys
385
```

<210> SEQ ID NO 4
<211> LENGTH: 389
<212> TYPE: PRT
<213> ORGANISM: Bacillus stearothermophilus GR75

<400> SEQUENCE: 4

```
Met Lys Arg Ile Gln Glu Phe Trp Tyr Cys Val Ala Ser Gln Glu Glu
1               5                   10                  15

Leu Pro Leu Tyr Lys Gly His Glu Ile Ser Ser Ser Val Cys Asp Asn
            20                  25                  30

Leu Leu Ala Phe Ile Glu His Tyr Lys Glu Glu Val Ser Lys Gly Lys
        35                  40                  45

Asn Leu Lys Thr Phe Leu Ser Glu Ala Leu Ile Lys Lys Pro Ser Ile
    50                  55                  60

Ile Asn His Leu Arg Leu Leu Gly Ile Ser Asp Lys Arg Leu Tyr
65                  70                  75                  80

Leu Asp Leu Thr Phe Ile Phe Asn Arg Ala Thr Thr Asp Asn Gly Glu
```

```
                     85                  90                  95
Arg Leu Leu Asn Glu Ser Arg Glu Asn Leu Val Lys His Asp Thr Lys
                100                 105                 110
Phe Phe Ile Asn Gln Leu Thr Asn Ser Asp Lys Lys Glu His Phe Ser
            115                 120                 125
Arg Leu Ile Thr Asp Tyr Phe Ile Asn Arg Gly Ile Glu Asp Ile Ile
        130                 135                 140
His Ile Phe Ser Arg Met Asp Lys Asn Gln Ile Thr Ser Ile Phe Asn
145                 150                 155                 160
Asn Leu Ile Ala Pro Lys Glu Ile Gln Gln Lys Gln Ala Lys Tyr Arg
                165                 170                 175
Gly His Gly Ala Glu Met Ala Phe Ala Lys Ile Phe His Asp Cys Gly
            180                 185                 190
Val Thr Ile Val Pro Glu Asn Lys His Ile Asn Pro Met Ala Gly Tyr
        195                 200                 205
Asp Pro Asn Val Asp Leu Thr Asn Met Thr Ile Val Pro Arg Asn Ala
    210                 215                 220
Ala Asn Arg Asn Ile His Ser Phe Asp Leu Val Val Lys Asp Asn Glu
225                 230                 235                 240
Gly Asn Ile Arg Val Leu Val Gln Ser Leu Ile His Ser Ser Asp Pro
                245                 250                 255
Gly Gln Tyr Gly Val Asn Lys Ser Asp Glu Thr Leu Glu Ile Lys Lys
            260                 265                 270
Leu Ile Asn Asn Tyr Asn Ser Arg Asn Ser Gln Lys Pro Val Tyr Leu
        275                 280                 285
Leu Gly Ser Val Asp Gly Val Gly Phe Cys Glu Asn Pro Asn Gly Thr
    290                 295                 300
Ile Val Lys Met Ile Asp Val Phe Asp Asp Phe Phe Gln Ile Asn Thr
305                 310                 315                 320
Leu Phe Lys Ile Pro Ile Phe Leu Gln Lys Ile Gly Leu Ile Asp Asn
                325                 330                 335
Val Lys Gly Ile Lys Phe Asp Thr Asp Phe Phe Asp Glu His Val Ile
            340                 345                 350
Glu Tyr Phe Glu Lys Thr Tyr Leu Lys Pro Ala Asn Ile Gln Asn Leu
        355                 360                 365
Thr Asn Ser Asn Cys Asn Phe Thr Asn Tyr Ile Lys Ala Gly Lys Gly
    370                 375                 380
Thr Val Ile Phe Lys
385

<210> SEQ ID NO 5
<211> LENGTH: 26
<212> TYPE: DNA
<213> ORGANISM: sequencing primer

<400> SEQUENCE: 5
actctgcaat ggcagccatt atgtta                                  26

<210> SEQ ID NO 6
<211> LENGTH: 24
<212> TYPE: DNA
<213> ORGANISM: sequencing primer

<400> SEQUENCE: 6
acattctcgg ctatgttggc tctc                                    24
```

```
<210> SEQ ID NO 7
<211> LENGTH: 24
<212> TYPE: DNA
<213> ORGANISM: sequencing primer

<400> SEQUENCE: 7
actgaaaatg gagaagtcga tgtg                                  24

<210> SEQ ID NO 8
<211> LENGTH: 24
<212> TYPE: DNA
<213> ORGANISM: sequencing primer

<400> SEQUENCE: 8
tatgcaatac agacatactt tagc                                  24

<210> SEQ ID NO 9
<211> LENGTH: 27
<212> TYPE: DNA
<213> ORGANISM: sequencing primer

<400> SEQUENCE: 9
actagataga gtcgatatta taatagg                               27

<210> SEQ ID NO 10
<211> LENGTH: 25
<212> TYPE: DNA
<213> ORGANISM: sequencing primer

<400> SEQUENCE: 10
gaaccacatg ttgggtctaa ataag                                 25

<210> SEQ ID NO 11
<211> LENGTH: 27
<212> TYPE: DNA
<213> ORGANISM: sequencing primer

<400> SEQUENCE: 11
cacattctcg gctatgttgg ctctctc                               27

<210> SEQ ID NO 12
<211> LENGTH: 26
<212> TYPE: DNA
<213> ORGANISM: sequencing primer

<400> SEQUENCE: 12
agaagcttat aaactagata gagtcg                                26

<210> SEQ ID NO 13
<211> LENGTH: 24
<212> TYPE: DNA
<213> ORGANISM: sequencing primer

<400> SEQUENCE: 13
ggcagaagtg attgagtttt attc                                  24

<210> SEQ ID NO 14
<211> LENGTH: 24
<212> TYPE: DNA
<213> ORGANISM: sequencing primer

<400> SEQUENCE: 14
aagcttataa actagataga gtcg                                  24
```

```
<210> SEQ ID NO 15
<211> LENGTH: 27
<212> TYPE: DNA
<213> ORGANISM: sequencing primer

<400> SEQUENCE: 15
aatccacctt gggttaactg ggagtac                                          27

<210> SEQ ID NO 16
<211> LENGTH: 24
<212> TYPE: DNA
<213> ORGANISM: sequencing primer

<400> SEQUENCE: 16
catttataag gcgagaacag gtgt                                             24

<210> SEQ ID NO 17
<211> LENGTH: 25
<212> TYPE: DNA
<213> ORGANISM: sequencing primer

<400> SEQUENCE: 17
cactgggggt gcgaacgctg tatac                                            25

<210> SEQ ID NO 18
<211> LENGTH: 24
<212> TYPE: DNA
<213> ORGANISM: sequencing primer

<400> SEQUENCE: 18
gtgtggagat atattgcaac tgag                                             24

<210> SEQ ID NO 19
<211> LENGTH: 24
<212> TYPE: DNA
<213> ORGANISM: sequencing primer

<400> SEQUENCE: 19
agtgatgtat attagcatgg atga                                             24

<210> SEQ ID NO 20
<211> LENGTH: 24
<212> TYPE: DNA
<213> ORGANISM: PCR primer

<400> SEQUENCE: 20
tcaaggtaaa gcctcttgtc agag                                             24

<210> SEQ ID NO 21
<211> LENGTH: 24
<212> TYPE: DNA
<213> ORGANISM: PCR primer

<400> SEQUENCE: 21
atagagctac cacagataat ggtg                                             24

<210> SEQ ID NO 22
<211> LENGTH: 24
<212> TYPE: DNA
<213> ORGANISM: PCR primer

<400> SEQUENCE: 22
```

```
gggttctcac aaaaacctac tcca                                          24
```

<210> SEQ ID NO 23
<211> LENGTH: 25
<212> TYPE: DNA
<213> ORGANISM: PCR primer

<400> SEQUENCE: 23

```
ggtacaatag tcaaaatgat agatg                                         25
```